(12) United States Patent
Anderson et al.

(10) Patent No.: US 9,320,891 B2
(45) Date of Patent: Apr. 26, 2016

(54) LEAD ANCHOR FOR IMPLANTABLE DEVICES AND METHODS OF MANUFACTURE AND USE

(75) Inventors: Meredith L. Anderson, Billerica, MA (US); Joshua D. Howard, Granada Hills, CA (US); Matthew J. Phillips, San Jose, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1860 days.

(21) Appl. No.: 12/416,801

(22) Filed: Apr. 1, 2009

(65) Prior Publication Data

US 2009/0254151 A1 Oct. 8, 2009

Related U.S. Application Data

(60) Provisional application No. 61/041,801, filed on Apr. 2, 2008.

(51) Int. Cl.
*A61N 1/05* (2006.01)
(52) U.S. Cl.
CPC *A61N 1/057* (2013.01); *A61N 1/05* (2013.01); *A61N 1/0558* (2013.01)
(58) Field of Classification Search
USPC .......................................... 607/116; 606/232
See application file for complete search history.

(56) References Cited

U.S. PATENT DOCUMENTS

| 4,276,882 A | 7/1981 | Dickhudt et al. |
|---|---|---|
| 4,462,401 A | 7/1984 | Burgio |
| 4,858,623 A | 8/1989 | Bradshaw et al. |
| 5,107,856 A * | 4/1992 | Kristiansen et al. .......... 607/126 |
| 5,152,298 A | 10/1992 | Kreyenhagen et al. |
| 5,158,097 A | 10/1992 | Christlieb |
| 5,163,911 A * | 11/1992 | Sirimanne et al. ....... 604/164.13 |
| 5,242,431 A | 9/1993 | Kristiansen |
| 5,628,780 A | 5/1997 | Helland et al. |
| 5,865,843 A | 2/1999 | Baudino |
| 6,181,969 B1 | 1/2001 | Gord |

(Continued)

FOREIGN PATENT DOCUMENTS

| EP | 0 085 417 B1 | 8/1983 |
|---|---|---|
| WO | WO-99/53994 | 10/1999 |

(Continued)

OTHER PUBLICATIONS

U.S. Appl. No. 11/238,240, filed Sep. 29, 2005.

*Primary Examiner* — Alyssa M Alter
(74) *Attorney, Agent, or Firm* — Lowe Graham Jones PLLC; Bruce E. Black

(57) ABSTRACT

A lead anchor includes a body with opposing first and second major surfaces and at least one edge surface between the first and second major surfaces. The body defines a first channel, a second channel, and a notch. The first channel extends from the edge surface of the body and is open at the first major surface. The second channel extends from the edge surface of the body and is open at the second major surface. The notch extends from the edge surface of the body, defines an opening from the first major surface through the body to the second major surface, and intersects the first channel and the second channel. The first channel, the second channel, and a portion of the notch define a passage through the body so that a lead can be inserted into the notch and turned to dispose a portion of the lead within the passage. The lead anchor can be part of a kit or system that also includes a lead.

20 Claims, 7 Drawing Sheets

(56) References Cited

U.S. PATENT DOCUMENTS

| | | |
|---|---|---|
| 6,192,279 B1 | 2/2001 | Barreras, Sr. et al. |
| 6,360,750 B1 | 3/2002 | Gerber et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,792,314 B2 | 9/2004 | Byers et al. |
| 6,847,849 B2 | 1/2005 | Mamo et al. |
| 6,901,287 B2 | 5/2005 | Davis et al. |
| 6,978,180 B2 | 12/2005 | Tadlock |
| 7,069,083 B2 | 6/2006 | Finch et al. |
| 7,072,719 B2 | 7/2006 | Vinup et al. |
| 7,343,202 B2 | 3/2008 | Mrva et al. |
| 7,447,546 B2 | 11/2008 | Kim et al. |
| 2001/0000187 A1 | 4/2001 | Peckham et al. |
| 2003/0078623 A1 | 4/2003 | Weinberg et al. |
| 2003/0114905 A1 | 6/2003 | Kuzma |
| 2003/0181900 A1* | 9/2003 | Long ............... 606/41 |
| 2003/0208247 A1 | 11/2003 | Spinelli et al. |
| 2004/0059392 A1 | 3/2004 | Parramon et al. |
| 2004/0116977 A1 | 6/2004 | Finch et al. |
| 2004/0230096 A1* | 11/2004 | Stefanchik et al. ........ 600/106 |
| 2005/0283202 A1 | 12/2005 | Gellman |
| 2005/0288760 A1 | 12/2005 | Machado et al. |
| 2006/0127158 A1 | 6/2006 | Olson et al. |
| 2006/0161235 A1 | 7/2006 | King |
| 2006/0206162 A1 | 9/2006 | Wahlstrand et al. |
| 2007/0050005 A1 | 3/2007 | Lauro |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0219595 A1 | 9/2007 | He |
| 2007/0239243 A1 | 10/2007 | Moffitt et al. |
| 2007/0255369 A1 | 11/2007 | Bonde et al. |
| 2008/0091255 A1 | 4/2008 | Caparso et al. |
| 2008/0140169 A1 | 6/2008 | Imran |
| 2008/0172116 A1 | 7/2008 | Mrva et al. |
| 2008/0183241 A1 | 7/2008 | Bedenbaugh |
| 2008/0183253 A1 | 7/2008 | Bly |
| 2008/0243220 A1 | 10/2008 | Barker |
| 2008/0312712 A1 | 12/2008 | Penner |

FOREIGN PATENT DOCUMENTS

| | | |
|---|---|---|
| WO | WO-00/13743 | 3/2000 |
| WO | WO-2004/054655 A1 | 7/2004 |
| WO | WO-2006/086363 A2 | 8/2006 |
| WO | WO-2007/056384 A2 | 5/2007 |
| WO | WO-2007/083108 A2 | 7/2007 |
| WO | WO-2007/149994 A2 | 12/2007 |
| WO | WO-2008/094789 A1 | 8/2008 |
| WO | WO-2008/121708 A2 | 10/2008 |

* cited by examiner

US 9,320,891 B2

LEAD ANCHOR FOR IMPLANTABLE DEVICES AND METHODS OF MANUFACTURE AND USE

CROSS REFERENCE TO RELATED APPLICATION

This application claims the benefit of U.S. Provisional Patent Application Ser. No. 61/041,801, filed Apr. 2, 2008, the entire contents of which is incorporated by reference.

FIELD

The invention is directed to lead anchors for implantable devices, as well as the implantable devices themselves and methods of manufacturing and using the implantable devices. The invention is also directed to lead anchors for implantable stimulation devices, as well as the implantable stimulation devices themselves and methods of manufacturing and using the implantable stimulation devices.

BACKGROUND

Implantable stimulation devices have been developed to provide therapy for a variety of disorders, as well as for other treatments. For example, implantable stimulation devices can be used to stimulate nerves (such as the spinal cord), muscles, or other tissue. An implantable stimulation device typically includes an implantable control module (with a pulse generator), one or more leads, and an array of stimulator electrodes on each lead. The stimulator electrodes are implanted in contact with or near the nerves, muscles, or other tissue to be stimulated. The pulse generator in the control module generates electrical pulses that are delivered by the electrodes to body tissue. As an example, electrical pulses can be provided to the dorsal column fibers within the spinal cord to provide spinal cord stimulation.

The stimulator electrodes are coupled to the control module by the lead and the control module is typically implanted elsewhere in the body, for example, in a subcutaneous pocket. The lead is often anchored at one or more places in the body to prevent or reduce movement of the lead or stimulator electrodes within the body which could damage tissue, move the stimulator electrodes out of the desired position, or interrupt the connection between the stimulator electrodes and the control module.

BRIEF SUMMARY

One embodiment is a lead anchor having a body with opposing first and second major surfaces and at least one edge surface between the first and second major surfaces. The body defines a first channel, a second channel, and a notch. The first channel extends from the edge surface of the body and is open at the first major surface. The second channel extends from the edge surface of the body and is open at the second major surface. The notch extends from the edge surface of the body, defines an opening from the first major surface through the body to the second major surface, and intersects the first channel and the second channel. The first channel, the second channel, and a portion of the notch define a passage through the body so that a lead can be inserted into the notch and turned to dispose a portion of the lead within the passage.

Another embodiment is a kit including at least a lead and the lead anchor.

Yet another embodiment is a system for stimulation including at least a control module, a lead comprising an array of electrodes coupled to the control module, and the lead anchor.

A further embodiment is a method of implanting a stimulation device. The method includes inserting a lead in a notch in a body of a lead anchor; and turning the lead to dispose a portion of the lead within a passage defined by a portion of the notch, a first channel and a second channel. The first and second channels extend from the notch to an edge surface of the body. The first channel is open from a first major surface of the body; and the second channel is open from a second major surface of the body with the second major surface being opposite the first major surface.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The invention is directed to lead anchors for implantable devices, as well as the implantable devices themselves and methods of manufacturing and using the implantable devices. The invention is also directed to lead anchors for implantable stimulation devices, as well as the implantable stimulation devices themselves and methods of manufacturing and using the implantable stimulation devices.

Figure 1:
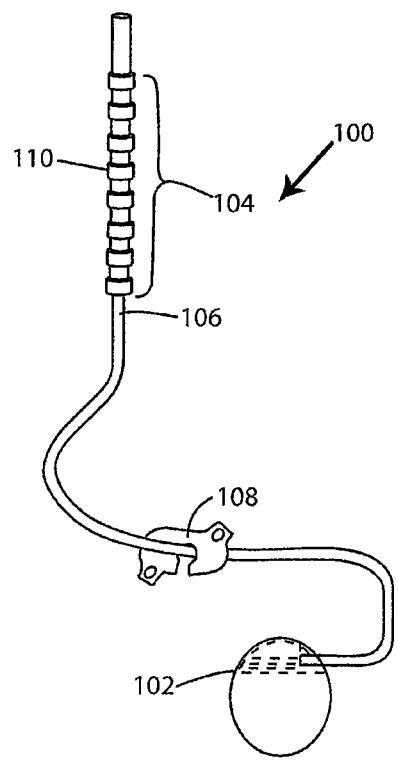
FIG. 1 is a schematic perspective view of one embodiment of a stimulator system, according to the invention.

FIG. 1 illustrates schematically an implantable stimulation device 100, such as a spinal cord stimulator. The implantable stimulation device includes a control module 102, an electrode array 104, a lead 106 coupling the control module to the electrode array, and one or more lead anchors 108. It will be understood that the system for stimulation can include more, fewer, or different components and can have a variety of different configurations including those configurations disclosed in the stimulator references cited herein. The control module 102 typically includes a pulse generator that provides pulses of stimulation current to electrodes of the electrode array 104. The control module 102 may also include a power source for generating the stimulation current or may receive power from an external source. The power source can be any available power source including batteries, such as primary batteries or rechargeable batteries. Examples of other power sources include, but are not limited to, super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

The control module 102 is optionally programmable to allow programming of one or more functions such as, for example, the selection of electrodes for stimulation, the selection of electrodes as anode or cathode, the amplitude of the stimulation current, the duration of the stimulation current, and the periodicity of the stimulation current. In some embodiments, the control module 102 can be accessed using a programming unit external to the body of the patient to alter or modify these functions.

The electrode array 104 typically includes two or more electrodes 110. In some embodiments, the electrode array 104 includes three, four, five, six, seven, eight, nine, ten or more electrodes 110.

Electrode leads include, for example, percutaneous leads, cuff leads, and paddle leads. Examples of stimulation systems with electrode leads are described in, for example, U.S. Pat. Nos. 6,181,969; 6,516,227; 6,609,029; 6,609,032; and 6,741,892; and U.S. patent applications Ser. Nos. 11/238,240; 11/319,291; 11/327,880; 11/375,638; 11/393,991; and 11/396,309, all of which are incorporated herein by reference.

The lead 106 includes a set of conductors (for example, one conductor per electrode of the electrode array) within a non-conductive sheathing. Each conductor couples one or more electrodes to each output node of the control module. Non-limiting examples of suitable control modules, electrode arrays, and leads are illustrated in U.S. Pat. Nos. 6,181,969; 6,516,227; 6,609,029; 6,609,032; and 6,741,892, all of which are incorporated herein by reference.

Other common, implantable devices include cardiac pacing leads, which typically may have one or two electrodes on the lead. Still other implantable devices include various implantable catheters or defribrillators. For example, one type of catheter is a drug delivery catheter for delivering drugs from a drug pump device attached to the delivery catheter. Any flexible, implantable lead or catheter may be attachable to tissue with an embodiment of the lead anchor herein described.

Figure 2:
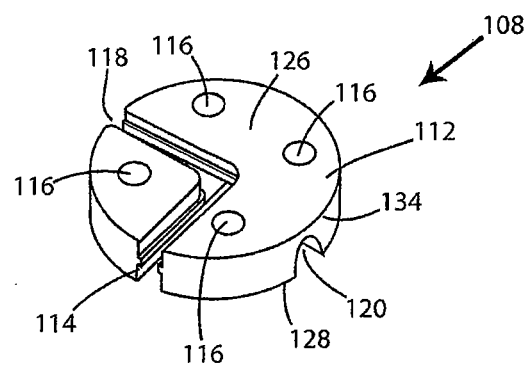
FIG. 2 is a schematic perspective view of one embodiment of a lead anchor, according to the invention.

A lead anchor can be used in an implantable device, such as an implantable stimulation device, to anchor a lead. For example, one or more lead anchors can be used to attach the lead(s) to surrounding tissue(s) to prevent or resist movement of the lead(s) within the body of the patient. FIG. 2 illustrates one embodiment of a lead anchor 108. The lead anchor includes a body 112 with a first major surface 126 and an opposing second major surface 128. The first major surface 126 and the second major surface 128 are preferably parallel to one another. The body 112 has at least one edge surface 134. The body defines a first channel 118, a second channel 120 and a notch 114. The lead anchor may also include one or more suture openings 116.

The body 112 of the lead anchor can have any shape including a circular, oval, elliptical, square, rectangular or irregular shape. The body 112 may be made of any biocompatible material. Preferably the material used to form the body 112 is durable and suitable for implantation in a patient over an expected period of time. Examples of suitable materials for the body 112 include polysulfone, polyolefins, silicone, polypropylene homopolymers and copolymers, Teflon™, and polyetheretherketone, as well as ceramics and metals (such as titanium or stainless steel). The body 112 may optionally be made of a radiopaque material. For example, the body 112 may include a radiologically dense material, such as tantalum powder as described in U.S. Pat. No. 5,628,780, which is herein incorporated by reference. The tantalum powder (e.g., 3-7% by weight) or other radiopaque material can be added to a polymer material used to form the body 112. The body 112 can also include a biocompatible coloring agent such as titanium dioxide that makes the lead anchor more readily visible to the naked eye. For example, the addition of 0.2-0.3% titanium dioxide by weight to the body 112 material may be used to make the lead anchor more readily visible.

The lead anchor 108 may be made by any process including, for example, molding. The lead anchor may be made of materials of different durometers or even using materials (such as metal) with hardness that is not typically measured in durometers. Moreover, portions of the lead anchor can be made using the same material but with different durometer values (e.g., polymer materials may be made with different durometer values). For example, the portions of the body 112 defining the first channel 118 or the second channel 120 or both may be made of a material with a higher durometer (harder material) than other portions of the lead anchor 108. The body 112 of the lead anchor 108 may optionally be coated with a material having a different durometer than the material used to make the body 112, for example by overmolding. For example, the body 112 can be coated with a material of a lower durometer (softer material) than the material used to make the body 112.

Figure 16:
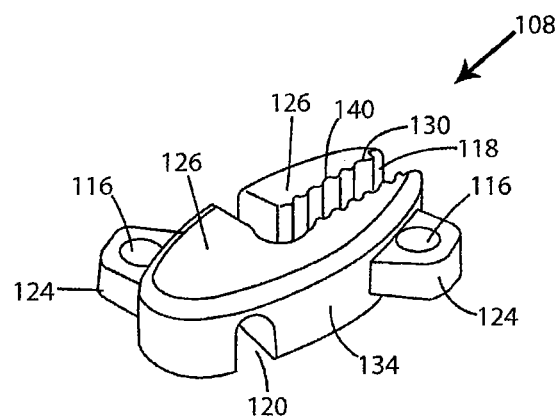
FIG. 16 is a schematic perspective view of one embodiment of a lead anchor, according to the invention.

Returning to FIG. 2, the first channel 118 extends from an edge surface 134 of the body 112 and is open at the first major surface 126. The second channel 120 extends from an edge surface 134 of the body 112 and is open at the second major surface 128 as illustrated schematically in FIG. 2. The first channel 118 and the second channel 120 may extend from any location on the edge surface 134. For example, the first channel 118 may extend from a location on the edge surface 134 that is opposite the location on the edge surface 134 from which the second channel 120 extends as illustrated schematically in, for example, FIGS. 2 and 3. Alternatively, the first channel 118 may extend from a location on the edge surface 134 that is not substantially opposite the location on the edge surface 134 from which the second channel 120 extends as illustrated schematically in FIG. 16.

As illustrated in FIG. 2, a notch 114 extends from an edge surface 134 of the body 112 and defines an opening from the first major surface 126 through the body 112 to the second major surface 128. The notch 114 intersects the first channel 118 and the second channel 120. The notch 114 is preferably configured and arranged to accept a portion of a lead.

The lead anchor 108 preferably includes one or more suture openings 116 that allow sutures to be used to fasten the lead anchor to the surrounding tissue. There may be one, two, three, four, five, six or more suture openings 116. The suture openings 116 may be disposed within the body 112 as illustrated schematically in FIG. 2. Alternatively or additionally, suture openings 116 may be disposed on one or more extensions 124 as illustrated schematically in FIGS. 3, 4, and 5.

Figure 17:
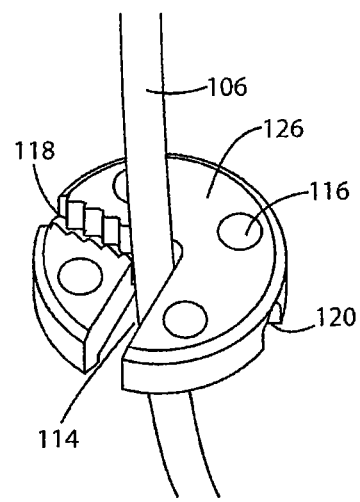
FIG. 17 is a schematic perspective view of one embodiment of a lead disposed in a notch of a lead anchor, according to the invention.

The lead anchor 108 can be used in a method of implanting a stimulation system. For example, the stimulation system may include a control module 102, a lead 106 including an electrode array 104, and a lead anchor 108. A portion of the lead 106 may be inserted into the notch 114 located in the body 112 of the lead anchor 108, for example, as illustrated schematically in FIG. 17. The lead anchor can be slid onto the lead from a proximal or distal end of the lead. Alternatively, the lead anchor can be placed at any location along the lead from the side, instead of sliding the lead anchor on the lead from an end of the lead. Once the lead is placed within the notch 114 of the lead anchor 108, the lead anchor can still be slid along the lead until it has been placed in the desired location.

Figure 18:
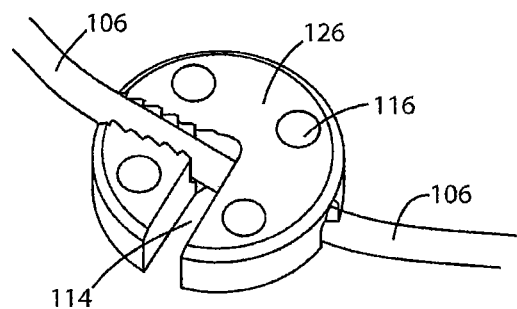
FIG. 18 is a schematic perspective view of one embodiment of a portion of a lead disposed in a passage of a lead anchor, according to the invention.

The lead may then be turned to dispose a portion of the lead within a passage 136 in the lead anchor 108 as illustrated schematically in FIG. 18. The passage 136 is defined by the notch 114, the first channel 118 and the second channel 120.

Figure 3:
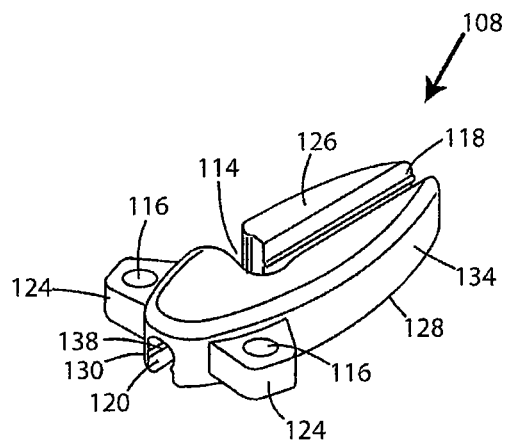
FIG. 3 is a schematic perspective view of one embodiment of a lead anchor, according to the invention.

FIG. 3 illustrates another embodiment of a lead anchor. This embodiment includes one or more extensions 124 with suture openings 116 for attaching the lead anchor to tissue. For example, one, two, three, four, or more extensions 124 may be present on the lead anchor 108. The extensions 124 can extend from one or more major surfaces (126, 128) or an edge surface 134 of the body 112. Preferably, the extensions 124 extend from an edge surface 134 of the body 112 as illustrated in FIG. 3 (and FIGS. 4 and 5). The extensions 124 can have any shape or size. Preferably, an extension 124 is shaped and sized such that a suture opening 116 may be disposed on the extension 124.

Extensions 124 can be disposed on the same side of the body 112 of the lead anchor 108. Preferably, extensions 124 are disposed on opposite sides of the body 112 of the lead anchor 108 as illustrated schematically in FIGS. 3, 4, 5, 9, 10 and 12. The extensions 124 can be disposed opposite from one another as illustrated in FIG. 3. Alternatively or additionally, an extension 124 can be disposed such that it is offset from another extension 124 on the opposite side of the body 112 as illustrated schematically in FIGS. 4, 5, 9, 10 and 12.

The embodiment of a lead anchor 108 illustrated schematically in FIG. 3 has a body 112 that is tapered at both ends. The body 112 of a lead anchor may alternatively be tapered at one end. Tapering of the body 112 may aid the insertion of the lead anchor into the patient such as, for example, into the supraspinous ligament of the patient.

Figure 4:
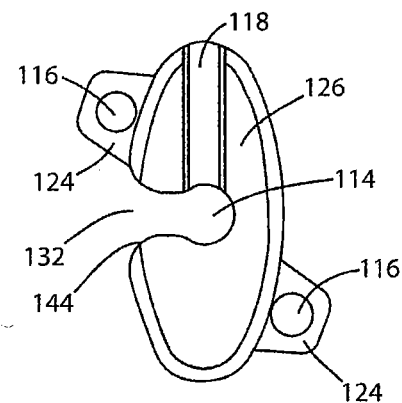
FIG. 4 is a schematic perspective top view of one embodiment of a lead anchor, according to the invention.

FIG. 4 schematically illustrates another embodiment of a lead anchor 108. This embodiment includes a body 112 with a rounded edge 144 at the lead insertion site 132, the site where the lead may be inserted into the notch 114. A rounded edge 144 at the lead insertion site 132 may aid placing a portion of the lead in the notch 114.

Figure 5:
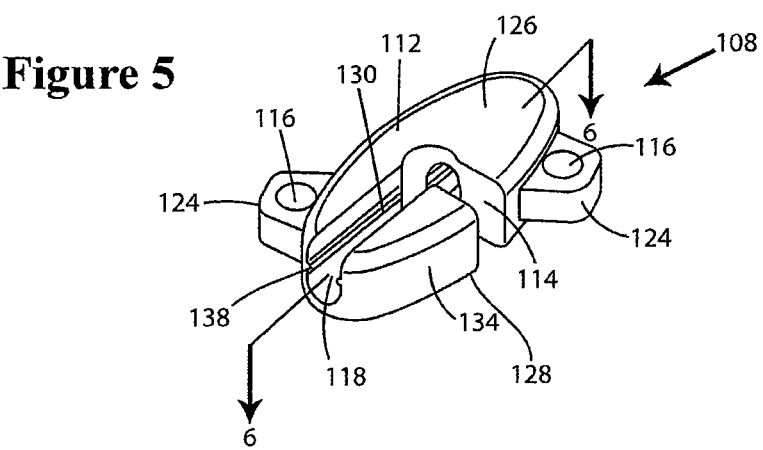
FIG. 5 is a schematic perspective view of one embodiment of a lead anchor, according to the invention.
Figure 6:
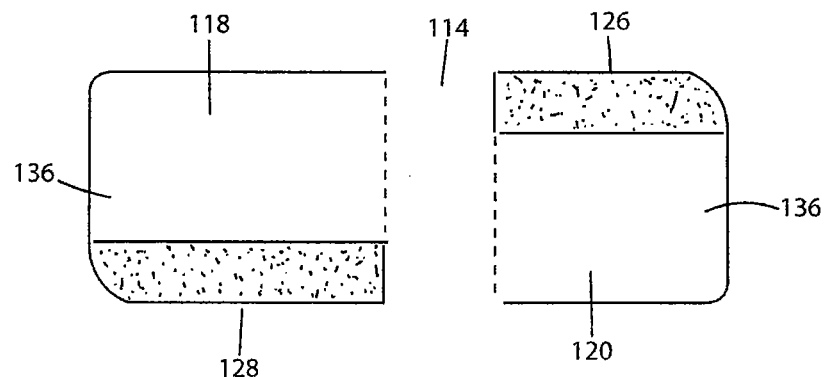
FIG. 6 is a schematic cross-sectional view of the lead anchor of FIG. 5 at line 6-6.
Figure 7:
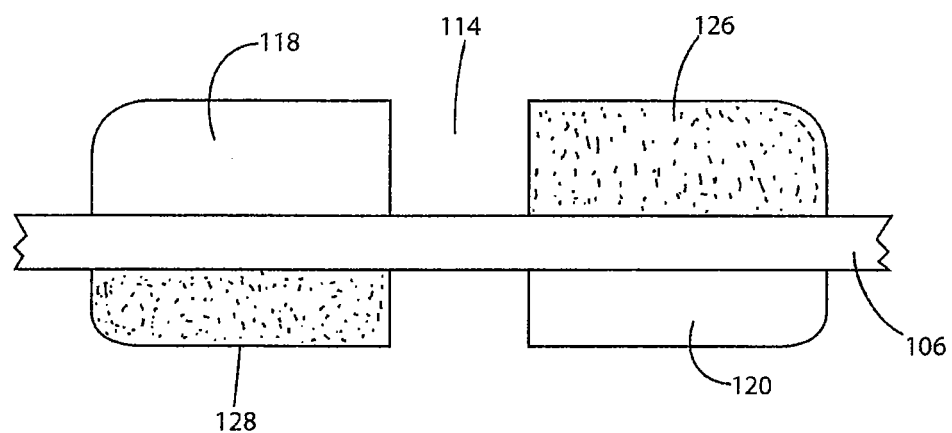
FIG. 7 is a schematic cross-sectional view of the lead anchor of FIG. 5 with one embodiment of a lead disposed in a passage of the lead anchor, according to the invention.
Figure 15:
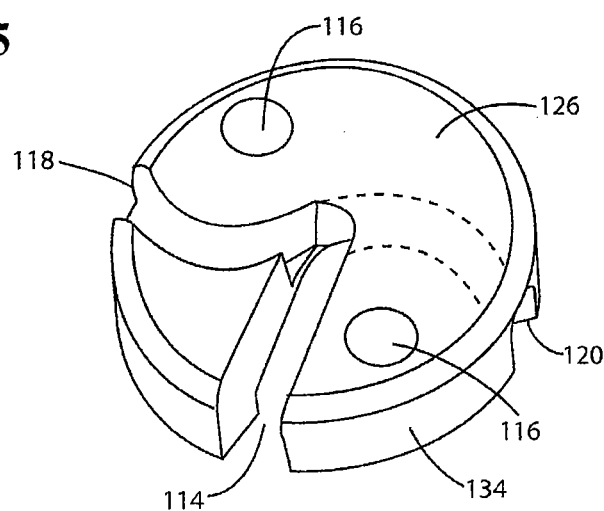
FIG. 15 is a schematic perspective view of one embodiment of a lead anchor, according to the invention.

FIG. 5 is a schematic representation of one embodiment of a lead anchor 108. FIG. 6 is a schematic cross-sectional view of the lead anchor of FIG. 5 at line 6-6 and schematically illustrates one embodiment of a passage 136. FIG. 7 schematically illustrates a cross sectional view of the lead anchor of FIG. 5 at line 6-6 with a portion of a lead 106 disposed in a passage of the lead anchor. The passage 136 can be substantially linear as illustrated schematically in, for example, FIGS. 3, 5 and 6. The passage 136 can also be non-linear as illustrated schematically in FIG. 15. For example, a non-linear passage 136 could be "S" shaped as illustrated in FIG. 15 or otherwise curved.

Figure 14:
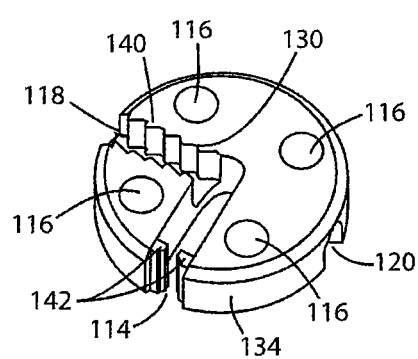
FIG. 14 is a schematic perspective view of one embodiment of a lead anchor, according to the invention.

A gate 142 may optionally be disposed in the notch 114 as illustrated schematically in FIG. 14. The gate 142 helps to keep the lead in the notch 114 and helps prevent the lead from being released from the lead anchor 108. The gate 142 can be made of any biocompatible material. For example, the gate 142 can be made of the same materials as the body 112. Alternatively, the gate 142 can be made of a material with a different durometer than the body 112 material. For example, the gate 142 may be made of a material with a higher durometer (harder material) or lower durometer (softer material) than the material used to make the body 112.

The first channel 118, the second channel 120 or both the first channel 118 and the second channel 120 may include one or more retention features 130 (see FIGS. 3, 5, 8, 9, 10, 11, 12, 13, 14 and 16). The retention features 130 may have several functions including retaining the lead within the first channel 118 or the second channel 120 and preventing or resisting movement of the lead within the lead anchor such as axial movement.

Figure 8:
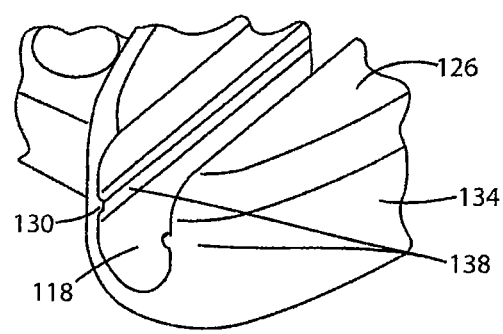
FIG. 8 is a close-up schematic perspective view of a portion of the lead anchor of FIG. 5.

The retention features 130 may take many different forms including, for example, one or more parallel retention features 138 as illustrated schematically in FIGS. 3, 5 and 8. Some embodiments of a parallel retention feature 138 are also illustrated schematically in the second channels 120 of the lead anchors of FIGS. 10, 11, and 12. Parallel retention features 138 are generally substantially parallel to the first major surface 126 or the second major surface 128. A retention feature is substantially parallel to the first major surface 126 or the second major surface 128 when the angle formed between the retention feature and the first major surface 126 or the second major surface 128 is from 0-40°, 0-30°, 0-20°, 0-10°, or 0-5°. Parallel retention features 138 help retain the lead within a channel of the lead anchor.

Figure 9:
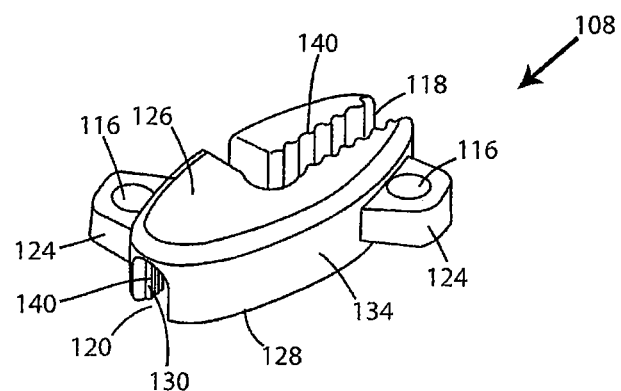
FIG. 9 is a schematic perspective view of one embodiment of a lead anchor, according to the invention.
Figure 10:
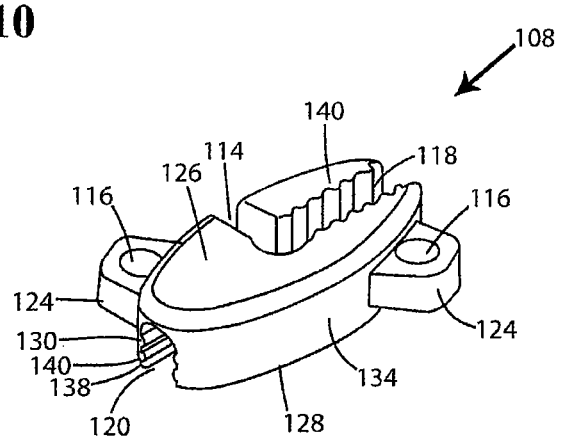
FIG. 10 is a schematic perspective view of one embodiment of a lead anchor, according to the invention.
Figure 11:
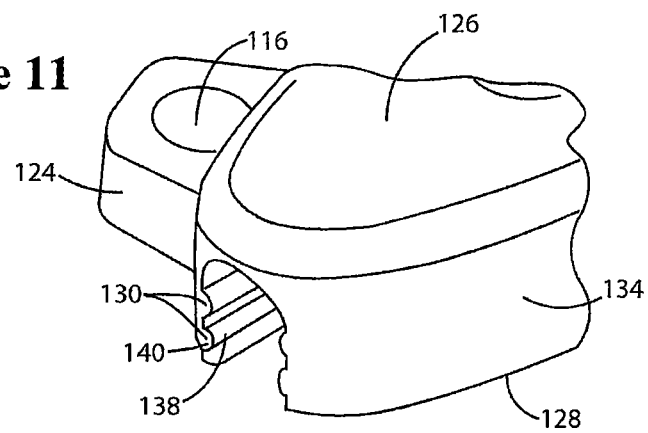
FIG. 11 is a close-up schematic perspective view of a portion of the lead anchor of FIG. 10.
Figure 12:
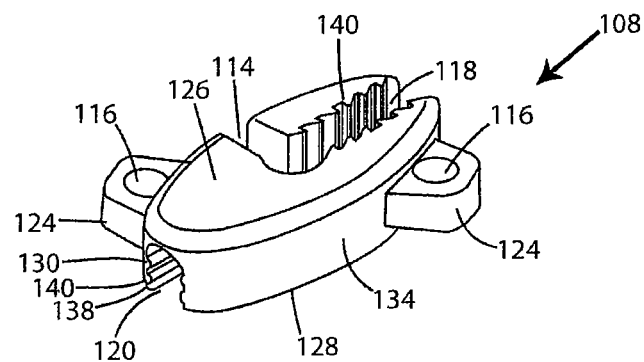
FIG. 12 is a schematic perspective view of one embodiment of a lead anchor, according to the invention.
Figure 13:
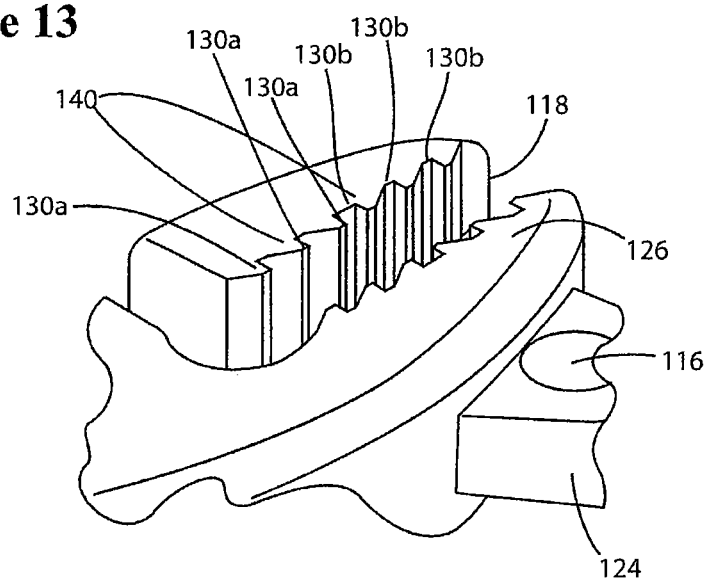
FIG. 13 is a close-up schematic perspective view of a portion of the lead anchor of FIG. 12.

FIGS. 9, 10, 11, 12, and 13 illustrate schematically further embodiments of lead anchors 108 with another type of retention feature. FIG. 11 is a close-up schematic view of a section of the lead anchor of FIG. 10. FIG. 13 is a close-up schematic view of a section of the lead anchor of FIG. 12. As illustrated in FIG. 9, the retention feature 130 can be a perpendicular retention feature 140. Perpendicular retention features 140 are disposed substantially perpendicular to the first major surface 126 or the second major surface 128. A retention feature is substantially perpendicular to the first major surface 126 or the second major surface 128 when the angle formed between the retention feature and the first major surface 126 or the second major surface 128 is from 50-90°, 60-90°, 70-90°, 80-90°, or 85-90°. Some embodiments of perpendicular retention features are illustrated schematically in the first channels 118 of the lead anchors 108 of FIGS. 9, 10, 12, 13, 14, and 16. Perpendicular retention features 140 prevent or reduce axial movement of the lead within the channels of the lead anchor.

The retention features 130 may have directionality, such as the "fin" shaped retention features 130 illustrated schematically in the first channels 118 of the lead anchors 108 of FIGS. 9, 10, 12 and 13. For example, the retention features 130 disposed in the first channel 118 of the lead anchor 108 of FIG. 10 have directionality and prevent or reduce axial movement of the lead toward the center of the lead anchor. The retention features 130 can be unidirectional, or oriented in a single direction, as illustrated for the retention features 130 in the first channel 118 of the lead anchor of FIG. 10. The retention features 130 can also be bidirectional, or oriented in two different directions, as illustrated for the retention features 130 in the first channels 118 of the lead anchors of FIGS. 12 and 13.

In FIG. 13, the retention features 130 in the first channel 118 are bi-directional; some of the retention features 130a are oriented in a first direction and some of the retention features 130b are oriented in a second direction. The retention features 130a prevent or reduce axial movement of the lead toward the center of the lead anchor (e.g., toward the notch). The retention features 130b prevent or reduce axial movement of the lead away from the center of the lead anchor.

The retention features 130 in the first channel 118, if any, can be the same or different than the retention features 130, if any, in the second channel 120. For example, the first channel 118 may include one or more parallel retention features 138 and the second channel 120 may include one or more perpendicular retention features 140. Alternatively, the first channel 118 may include one or more perpendicular retention features 140 and the second channel may include one or more parallel retention features 138 (see, e.g., FIG. 10). Optionally, the first channel 118 may include bidirectional retention features 130 and the second channel 120 may include uni-directional retention features 130. The first channel 118 and the second channel 120 may also both include uni-directional retention features 130, but the retention features in each channel could be oriented in the same or opposite directions.

Figure 19:
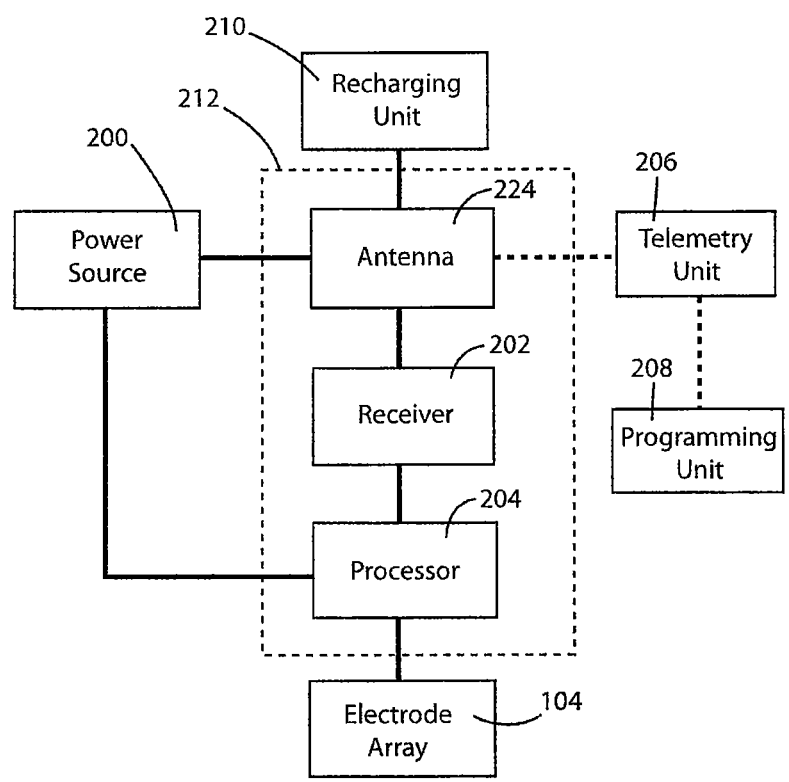
FIG. 19 is a schematic overview of components of a system for stimulation, according to an embodiment of the invention.

FIG. 19 is a schematic overview of one embodiment of components of a system for stimulation, including an electronic subassembly 212 (which may or may not include the power source 200), according to the invention. It will be understood that the system for stimulation and the electronic subassembly 212 can include more, fewer, or different components and can have a variety of different configurations including those configurations disclosed in the stimulator references cited herein. Some or all of the components of the system for stimulation can be positioned on one or more circuit boards or similar carriers within a housing of a stimulator, if desired.

Any power source 200 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 224 or a secondary antenna. The external power source can be in a device that is mounted on the skin of the user or in a unit that is provided near the stimulator user on a permanent or periodic basis.

If the power source 200 is a rechargeable battery, the battery may be recharged using the optional antenna 224, if desired. Power can be provided to the battery for recharging by inductively coupling the battery through the antenna to a recharging unit 210 (see FIG. 19) external to the user. Examples of such arrangements can be found in the stimulator references identified above.

In one embodiment, electrical current is emitted by the electrodes 110 to stimulate motor nerve fibers, muscle fibers, or other body tissues near the stimulator. The electronic subassembly 212 provides the electronics used to operate the stimulator and generate the electrical pulses at the electrodes 110 to produce stimulation of the body tissues. FIG. 19 illustrates one embodiment of components of the electronic subassembly and associated units.

In the illustrated embodiment, a processor 204 is generally included in the electronic subassembly 212 to control the timing and electrical characteristics of the stimulator. For example, the processor can, if desired, control one or more of the timing, frequency, strength, duration, and waveform of the pulses. In addition, the processor 204 can select which electrodes can be used to provide stimulation, if desired. In some embodiments, the processor may select which electrode(s) are cathodes and which electrode(s) are anodes. In some embodiments with electrodes disposed on two or more sides of the housing, the processor may be used to identify which electrodes provide the most useful stimulation of the desired tissue. This process may be performed using an external programming unit, as described below, that is in communication with the processor 204.

Any processor can be used and can be as simple as an electronic device that produces pulses at a regular interval or the processor can be capable of receiving and interpreting instructions from an external programming unit 208 that allows modification of pulse characteristics. In the illustrated embodiment, the processor 204 is coupled to a receiver 202 which, in turn, is coupled to the optional antenna 224. This allows the processor to receive instructions from an external source to direct the pulse characteristics and the selection of electrodes, if desired.

In one embodiment, the antenna 224 is capable of receiving signals (e.g., RF signals) from an external telemetry unit 206 which is programmed by a programming unit 208. The programming unit 208 can be external to, or part of, the telemetry unit 206. The telemetry unit 206 can be a device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the stimulator. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 224 and receiver 202 can be used to modify or otherwise direct the operation of the stimulator. For example, the signals may be used to modify the pulses of the stimulator such as modifying one or more of pulse duration, pulse frequency, pulse waveform, and pulse strength. The signals may also direct the stimulator to cease operation or to start operation or to start charging the battery. In other embodiments, the electronic subassembly 212 does not include an antenna 224 or receiver 202 and the processor operates as programmed.

Optionally, the stimulator may include a transmitter (not shown) coupled to the processor and antenna for transmitting signals back to the telemetry unit 206 or another unit capable of receiving the signals. For example, the stimulator may transmit signals indicating whether the stimulator is operating properly or not or indicating when the battery needs to be charged. The processor may also be capable of transmitting information about the pulse characteristics so that a user or clinician can determine or verify the characteristics.

The optional antenna 224 can have any form. In one embodiment, the antenna comprises a coiled wire that is wrapped at least partially around the electronic subassembly within or on the housing.

Any method of manufacture of the components of the system for stimulation can be used. For example, the power source and antenna can be manufactured as described in U.S. Patent Application Publication No. 2004/0059392. These components can then be placed inside the housing (or, alternatively, the housing can be formed, e.g., molded, around the components).

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor comprising:
a body having opposing first and second major surfaces and at least one edge surface between the first and second major surfaces, the body defining a first lead channel, a second lead channel, and a notch wherein
the first lead channel extends from the edge surface of the body and is open at the first major surface;
the second lead channel extends from the edge surface of the body and is open at the second major surface;
the notch extends from the edge surface of the body, defines an opening from the first major surface through the body to the second major surface, and intersects the first lead channel and the second lead channel; and
the first lead channel, the second lead channel, and a portion of the notch define a passage through the body wherein the body is configured and arranged so that a lead can be inserted into the notch and turned to dispose a portion of the lead within the passage with the lead extending along the first lead channel and along the second lead channel.

2. The lead anchor of claim 1, further comprising at least one retention feature disposed within the first lead channel, the second lead channel or both the first lead channel and the second lead channel.

3. The lead anchor of claim 2, wherein the at least one retention feature comprises a parallel retention feature with a ridge that is configured and arranged to run substantially parallel to the portion of the lead disposed in the first or second lead channel within which the parallel retention feature is disposed.

4. The lead anchor of claim 2, wherein the at least one retention feature comprises a perpendicular retention feature with a ridge that is configured and arranged to run substantially perpendicular to the portion of the lead disposed in the first or second lead channel within which the perpendicular retention feature is disposed.

5. The lead anchor of claim 2, wherein the at least one retention feature comprises a uni-directional retention feature with a peak that is configured and arranged to run substantially perpendicular to the portion of the lead disposed in the first or second lead channel within which the uni-directional retention feature is disposed, wherein the peak is oriented to prevent or reduce axial movement of the portion of the lead toward a center of the lead anchor.

6. The lead anchor of claim 2, wherein the at least one retention feature comprises a plurality of retention features with peaks that are configured and arranged to run substantially perpendicular to the portion of the lead disposed in the first or second lead channel within which the retention feature is disposed, wherein the peaks are oriented to provide bi-directional retention to prevent or reduce axial movement of the portion of the lead both toward and away from a center of the lead anchor.

7. The lead anchor of claim 2, wherein the at least one retention feature comprises a retention feature disposed within the second lead channel and a retention feature disposed within the first lead channel.

8. The lead anchor of claim 2, wherein the at least one retention feature comprises a first retention feature and a second retention feature, wherein the first retention feature is disposed within the first lead channel and has a peak oriented in an opposite direction to a peak of the second retention feature which is disposed within the second lead channel.

9. The lead anchor of claim 1, further comprising at least one suture opening.

10. The lead anchor of claim 1, wherein at least one end of the body is tapered.

11. The lead anchor of claim 1, wherein the body has a rounded edge at a lead insertion site.

12. The lead anchor of claim 1, further comprising a gate feature disposed in the notch, the gate feature extending away from a remainder of the lead anchor and into the notch and configured and arranged to prevent the lead from being released from the lead anchor.

13. The lead anchor of claim 9, further comprising an extension, wherein the at least one suture opening is disposed on the extension.

14. The lead anchor of claim 1, wherein the body comprises a radiopaque material.

15. The lead anchor of claim 1, wherein the passage through the body formed by the first lead channel, the second lead channel and a portion of the notch is non-linear.

16. A kit comprising:
a lead; and
the lead anchor of claim 1.

17. A system for stimulation comprising:
a control module;
a lead comprising an array of electrodes coupled to the control module; and
at least one lead anchor that may be disposed around a portion of the lead, wherein the lead anchor comprises
a body having opposing first and second major surfaces and at least one edge surface between the first and second major surfaces, the body defining a first lead channel, a second lead channel, and a notch wherein
the first lead channel extends from the edge surface of the body and is open at the first major surface;
the second lead channel extends from the edge surface of the body and is open at the second major surface;
the notch extends from the edge surface of the body, defines an opening from the first major surface through the body to the second major surface, and intersects the first lead channel and the second lead channel; and the first lead channel, the second lead channel, and a portion of the notch define a passage through the body wherein the body is configured and arranged so that a lead can be inserted into the notch and turned to dispose a portion of the lead within the passage with the lead extending along the first lead channel and along the second lead channel.

18. A method of implanting a stimulation device, the method comprising:

inserting a lead in a notch in a body of a lead anchor; and turning the lead to dispose a portion of the lead within a first lead channel and a second lead channel, wherein the first and second lead channels extend from the notch to an edge surface of the body; the first lead channel is open from a first major surface of the body; and the second lead channel is open from a second major surface of the body, the second major surface being opposite the first major surface.

19. The method of implanting a stimulation device of claim 18, further comprising sliding the lead anchor along the lead until it has been placed in the desired location after inserting the lead in the notch and before turning the lead to dispose a portion of the lead within the passage.

20. The method of implanting a stimulation device of claim 18, wherein inserting a lead in a notch in a body of a lead anchor comprises inserting a portion of the lead between a proximal end and a distal end of the lead in the notch.

* * * * *